(12) United States Patent
Inoue et al.

(10) Patent No.: US 6,853,357 B2
(45) Date of Patent: Feb. 8, 2005

(54) IMAGE DISPLAY APPARATUS AND METHOD, AND STORAGE MEDIUM

(75) Inventors: Hitoshi Inoue, Kanagawa (JP); Shigeru Sanada, Ishikawa (JP)

(73) Assignee: Canon Kabushiki Kaisha, Tokyo (JP)

(*) Notice: Subject to any disclaimer, the term of this patent is extended or adjusted under 35 U.S.C. 154(b) by 301 days.

(21) Appl. No.: 09/923,199

(22) Filed: Aug. 6, 2001

(65) Prior Publication Data

US 2002/0050986 A1 May 2, 2002

(30) Foreign Application Priority Data

Aug. 11, 2000 (JP) ........................................ 2000-245384

(51) Int. Cl.[7] .......................... H04N 15/00; G06K 9/00; G09G 5/00
(52) U.S. Cl. ............................... 345/9; 348/52; 382/181
(58) Field of Search ................................. 382/131, 132, 382/154, 128, 181, 204, 215; 348/42, 51, 52, 54, 55; 353/6, 7; 356/12, 14; 378/41, 42; 345/7, 8, 9

(56) References Cited

U.S. PATENT DOCUMENTS

| | | | | |
|---|---|---|---|---|
| 5,155,750 A | * | 10/1992 | Klynn et al. | .................. 378/42 |
| 5,163,076 A | * | 11/1992 | Koyama | ....................... 378/42 |
| 5,233,639 A | * | 8/1993 | Marks | .......................... 378/41 |
| 6,181,768 B1 | * | 1/2001 | Berliner | ....................... 378/41 |

* cited by examiner

*Primary Examiner*—Chanh Nguyen
*Assistant Examiner*—Paul Bell
(74) *Attorney, Agent, or Firm*—Cowan, Liebowitz & Latman

(57) ABSTRACT

There are provided an image display apparatus and an image display method, which are capable of clearly indicating to an observer subtle differences between two images of the same subject obtained at different times, without the need for complex image processing, and a storage medium storing a program for implementing the image display method. Two images of the same subject obtained at different times are inputted. A stereo display device displays the two inputted images in a manner enabling an observer to fuse the two inputted images together for stereoscopic viewing. A control means controls the stereo display device to display the two inputted images such that the two images are projected separately into the left and right eyes of the observer.

46 Claims, 12 Drawing Sheets

IMAGE DISPLAY APPARATUS AND METHOD, AND STORAGE MEDIUM

BACKGROUND OF THE INVENTION

1. Field of the Invention

The present invention relates to an image display apparatus and image display method for displaying two images of the same subject obtained, for example, at different times, and a storage medium storing a program for implementing the image display method.

2. Prior Art

Medical X-ray images, in particular X-ray images of the human chest, are indispensable to medical diagnosis, and are very widely used even today.

Chest X-ray images are used for examining the extent of progress of a disease or for examining for changes indicative of outbreak of a disease in a patient who is the subject of the X-ray radiography. Such examinations are often carried out by comparing current and past X-ray images of the same patient. In such a comparison, the past image and the current image are generally displayed simultaneously or films thereof are presented simultaneously, and an observer looks for differences between the two.

Moreover, as described in "Application of digital image change detection to diagnosis and follow-up of cancer involving the lungs; Kinsey, J. H. and Vannelli, B. D.; SPIE70: 99-112; 1975", attempts are being made to develop a method in which a differential image between a past image and a current image is generated and this differential image is viewed, thus allowing the differences between the past image and the current image to be seen clearly. Research into making this method fit for practical use is still in progress.

A specific problem being researched is how to cope with changes in the radiographic conditions between the past image and the current image. In particular, the positional relationship between the X-ray source, the radiographic subject and the image receiving section may vary greatly due to differences in the radiographic environment and the radiographer between the past radiography session and the current radiography session.

As a result, the straightforward difference between the past image and the current image may indicate changes in the position from which the X-ray was taken rather than changes in the lung field as intended. A technique commonly used at present is called "image warping", which involves paying attention to the shape of the ribs in particular in the past image or the current image and warping the image, thus allowing the difference between the two images to be obtained with improved accuracy (the shadow of the ribs is eliminated upon taking the difference) (see, for example "Digital chest radiography: Effect of temporal subtraction images on detection accuracy; Difazio, M. C., MacMahon, H. M., Xu X-W., et al.; Radiology 202: 447–452; 1997").

Moreover, from the standpoint that eliminating the shadow of the ribs is different to observing changes in the shadow of the lung field, which is the original objective, an alternative method has been devised in which attention is not paid to the ribs, but rather only the lung markings are extracted from the images and the difference between the images is obtained by aligning the lung markings (see "Hai-monri o taishou to shita gazou-ichi-awase-hou—Kyoubu X-sen gazou no jikanteki-sabun-hou (Image alignment method targeting lung markings—Temporal difference method for chest X-ray images); Sanada et al.; Japanese Journal of Radiological Technology; Vol. 56, No. 3, 398–404; 2000").

However, the radiographic subject is generally 3-dimensional having depth, but the radiographed image is only a 2-dimensional projection of the radiographic subject. Regardless of how this projected image which gives only 2-dimensional information is changed through warping, it is thus fundamentally impossible to obtain the difference between two images in 3 dimensions. Moreover, image warping generally requires complex image processing steps, and thus a great deal of computation.

SUMMARY OF THE INVENTION

It is an object of the present invention to provide an image display apparatus and an image display method, which are capable of clearly indicating to an observer subtle differences between two images of the same subject obtained at different times, without the need for complex image processing, and a storage medium storing a program for implementing the image display method.

To attain this object, according to the present invention, there is provided an image display apparatus comprising input means for inputting two images of the same subject obtained at different times, display means for displaying the two inputted images in a manner enabling an observer to fuse the two inputted images together for stereoscopic viewing, and display control means for controlling the display means to display the two inputted images such that the two images are projected separately into the left and right eyes of the observer.

In a preferred embodiment of the present invention, the image display apparatus comprises position designation means for designating a position on the display screen of the display means in accordance with operational input from the observer, and the display control means is responsive to a position being designated by the position designation means, for controlling the display means to display a mark in the designated position on the display screen of the display means in a manner being superposed on each of the two images.

Preferably, each of the two images is an image produced from a radiation intensity distribution.

Also preferably, the two images are a past image and a current image taken of the same human subject.

Preferably, the image display apparatus according to the present invention comprises spatial frequency accentuation means for carrying out spatial frequency accentuation processing on the images, and the display control means controls the display means to display the images subjected to the spatial frequency accentuation processing.

More preferably, the image display apparatus according to the present inventiuon comprises spatial frequency intensity setting means for setting a spatial frequency intensity of the spatial frequency accentuation processing in accordance with operational input from the observer, and the spatial frequency accentuation means carries out the spatial frequency accentuation processing on the images at the set spatial frequency intensity.

In another preferred embodiment, the display means has a color display function, and the display control means controls the display means to display the two images while changing colors of the two images independently.

In a further preferred embodiment, the display control means controls the display means to display the two images while making one of the two images flash.

The flashing interval at which the one of the two images is made to flash is variable.

In a still further preferred embodiment, the display means has a display screen, and wherein the display control means controls the display means to carry out rotating, magnifying and shifting at least one of the two images on the display screen of the display means.

In an advantageous embodiment, the image display apparatus according to the present invention comprises at least two single image display means for displaying each of the two images singly, and the display control means controls the single image display means to display each of the two images singly.

Advantageously, when the mark is displayed in the position designated by the position designation means on the display screen of the display means, the display control means controls the single image display means to also display the mark in a position corresponding to the designated position on the display screen of each of the at least two single image display means.

More advantageously, the image display apparatus according to the present invention comprises storage means for separately storing each of the two images along with position information indicating the corresponding position of the mark.

To attain the above object, the present invention also provides an image display method of displaying two images of the same subject obtained at different times on display means in a manner such that an observer can fuse the two images together for stereoscopic viewing, the method comprising the steps of inputting the two images, and controlling the display means to display the two inputted images such that the two inputted images are projected separately into left and right eyes of the observer, whereby the observer can fuse the images together.

To attain the above object, the present invention further provides a storage medium storing, so as to be readable by an information processing apparatus, a program for constructing an image display system for displaying two images of the same subject obtained at different times on display means in a manner such that an observer can fuse the two images together for stereoscopic viewing, the program comprising an input module for inputting the two images, and a display control module for controlling the display means to display the two inputted images such that the two inputted images are projected separately into left and right eyes of the observer, whereby the observer can fuse the images together.

To attain the above object, the present invention also provides an image display apparatus comprising storage means for storing a plurality of images of the same subject along with information relating to a correspondence relationship between the images and times when the images were taken, searching means for searching for images having a correspondence relationship therebetween from the plurality of images stored in the storage means, display means for displaying two of the images in a manner enabling an observer to fuse the two images together for stereoscopic viewing, and display control means for reading any two of the images from the storage means and controlling the display means to display the read two images.

Preferably, the display control means includes image processing means for carrying out different image processing on each of the two images displayed on the display means.

For example, the image processing means carries out processing to make the two images different in color.

Alternatively, the image processing means carries out processing to make one of the two images flash.

Preferably, the display control means causes search results from the searching means to be displayed as a list of reduced images, and controls the display means to stereoscopically display two images selected from the displayed list.

To attain the above object, the present invention further provides an image display method comprising a storage step of storing a plurality of images of the same subject along with information relating to a correspondence relationship between the images and times when the images were taken, a searching step of searching for images having a correspondence relationship therebetween from the stored images, a first display step of displaying results of the search, and a second display step of displaying any two images selected from the search results so as to be viewable as a stereoscopic image.

The above and other objects, features and advantages of the invention will become more apparent from the following detailed description taken in conjunction with the accompanying drawings.

DETAILED DESCRIPTION OF PREFERRED EMBODIMENTS

Embodiments of the present invention will now be described with reference to the drawings.

Figure 9:
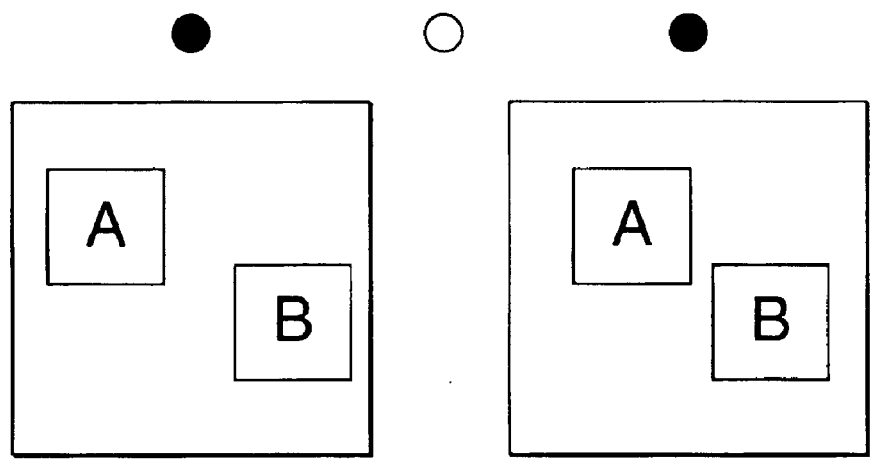
FIG. 9 shows an example of images viewed using a crossover method.
Figure 10:
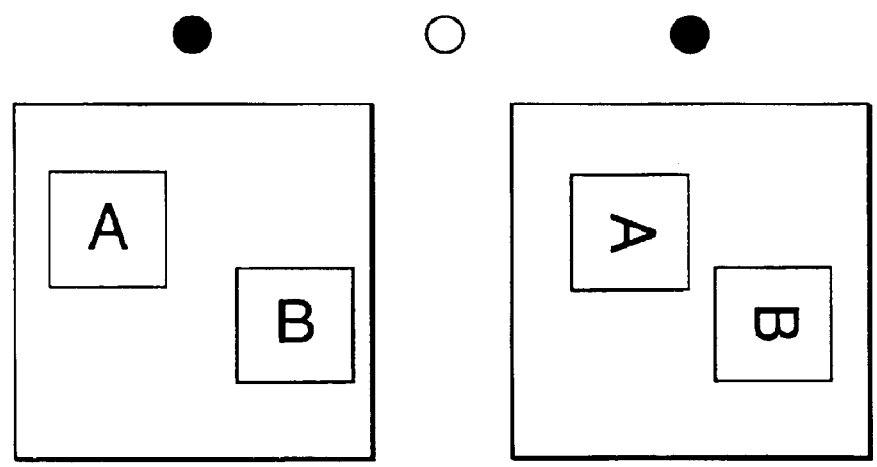
FIG. 10 shows another example of images viewed using the crossover method.

First, the principles behind the present invention will be described. FIGS. 9 and 10 each show an example of images viewed using a crossover method.

According to the present invention, two images of the same subject obtained at different times are inputted, and display means is controlled to display the two images such that the two inputted images are projected separately into the left and right eyes of an observer. As a result, the two images displayed on the display means are fused together by the observer to be viewed stereoscopically by the observer.

When looking for differences between two images of the same subject, a technique is generally used in which the two images are placed, for example, side by side, and are viewed stereoscopically with the naked eyes using the so-called crossover method or the so-called parallel method. In this technique, the two images are fused together by the observer and perceived as a single image. Fusion is difficult to achieve in places where the images differ-from one another, giving the observer a feeling of incongruity. It is this feeling of incongruity that allows the observer to find discrepancies between the two images.

The basis of determining a 3-dimensional structure using both eyes is fusion of the images captured by either eye. When viewing the same subject with both eyes, the image captured by the left eye and the image captured by the right eye are fundamentally images of the same subject. However, parallax occurs due to the eyes being in different positions from one another, with the positions (phases) of the captured images varying according to the 3-dimensional structure of the subject. That is, the images seen by the left and right eyes are almost the same, but there are differences in the positions of the image segments thereof. A human fuses the two images together and perceives them as a single image, and moreover judges intuitively (i.e. through his/her advanced processing ability) 3-dimensional position (i.e. depth) from differences in position of the same-shaped object between the left eye image and the right eye image.

In other words, a human interprets images captured by the left and right eyes as being of the same subject, and moreover automatically judges differences between the two images as being due to 3-dimensional depth, and creates a corresponding 3-dimensional image in the brain.

For example, when the images shown in FIG. 9 are viewed using the crossover method, the image on the left is seen by the right eye and the image on the right by the left eye. If the points ● above the images are perceived as overlapping at the central point ○ in the fused image created in the observer's brain, then the observer should perceive the square having A written therein (hereinafter referred to as the "A square") as jumping out at him/her and the square having B written therein (hereinafter referred to as the "B square") as being positioned further back.

The A square and the B square are actually shifted sideways to different positions in the two images relative to the large enclosing square frame. However, a human fuses the two images into one, and intuitively judges the A square in each of the images to be the same object and the B square in each of the images to be the same object.

In the case of the two images shown in FIG. 10, however, the orientations of the letters A and B differ between the two images. The human observer tries to fuse the two images but can only do so to a limited extent, and thus experiences a strong feeling of incongruity.

Figure 11:
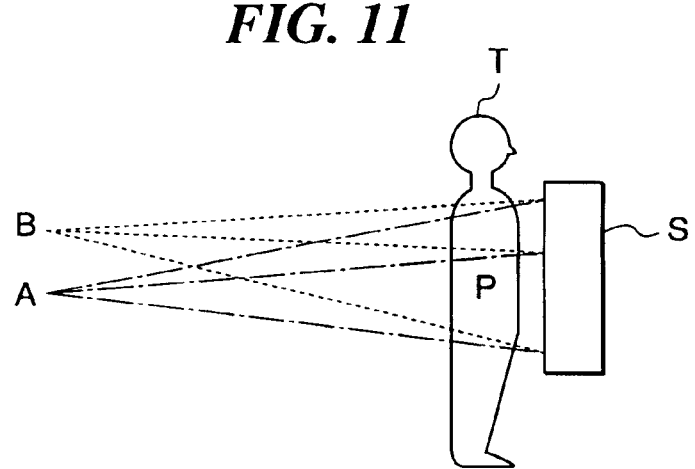
FIG. 11 is a schematic view of X-ray radiography of the chest of a human.
Figure 12:
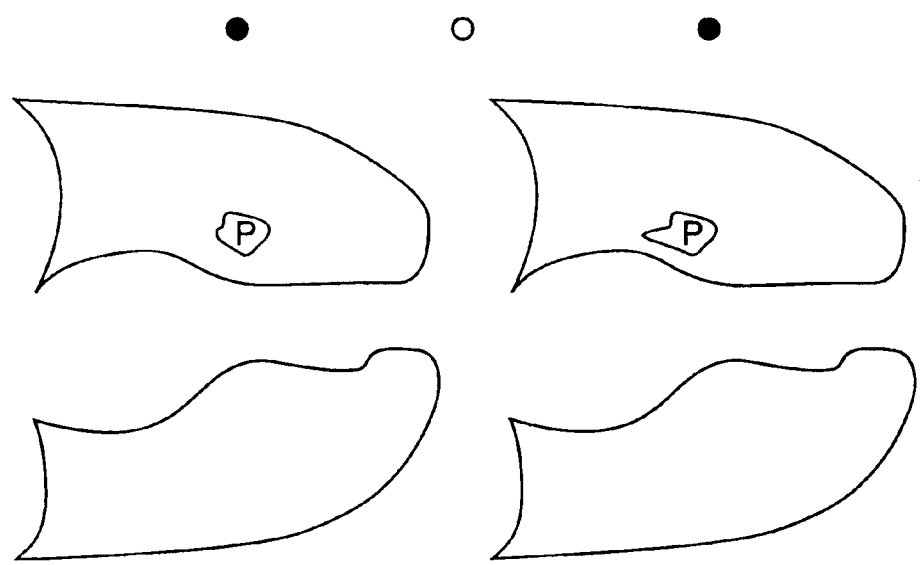
FIG. 12 shows an example in which chest X-ray radiographs are displayed rotated through 90 degrees.

Moving on, a description will now be given of the case of two chest X-ray images taken of the same subject at different times, with reference to FIGS. 11 and 12. FIG. 11 is a schematic view of X-ray radiography of the chest of a human, and FIG. 12 shows an example in which chest X-ray radiographs are displayed rotated through 90 degrees. As shown in FIG. 11, the chest X-ray radiography equipment is constituted such that an X-ray source is positioned in position A or B, X-rays are radiated out towards a subject, namely a human body T, and a chest X-ray image is obtained by an image receiver S. It shall be assumed here that a chest X-ray image of the human body T was obtained on a past occasion with the X-ray source at position A and on a current occasion with the X-ray source at position B.

In this case, the position at which an object P in the human body appears on the image differs between the past image and the current image as shown in FIG. 12. Generally, in chest X-ray radiography, the subject is made to stand in the center of the image receiver S, and then the X-ray source (an X-ray tube) is aligned with the center of the image receiver S and the X-ray is taken. In such a case, the X-ray source and the image receiver S rarely shift relative to one another in the sideways direction, but often shift relative to one another in the vertical direction as shown in FIG. 11. Moreover, even if the positional relationship between the X-ray source and the image receiver S is unchanged between the past image and the current image, there will be somewhat of a difference in the posture of the subject.

In a case as described above, the two chest X-ray images (the past image and the current image) are generally viewed rotated through 90 degrees as shown in FIG. 12. If viewing is carried out using the crossover method (or the parallel method) such that the points ● above the images are perceived as overlapping at the central point ○ in the fused image created in the observer's brain, then any difference in the position of the object P in the chest between the two images will be perceived as 3-dimensional depth, while any difference in the shape of the object P between the two images will be observed as a feeling of incongruity.

If the above method is used, then differences between the two images can be clearly shown merely by utilizing the observer's own inherent, intuitive, advanced processing ability; it is not necessary to generate a differential image, even without the need for generating a differential image. Note, however, that viewing using this crossover method (or parallel method) is not actually carried out in everyday life, and hence adequate training is required to become proficient.

In general, if, as in the present invention, a past image and a current image are viewed simultaneously using some kind of stereo display device, then differences between the two images can be perceived as incongruities in the fused 3-dimensional image without a great deal of skill being required. Display methods allowing such stereoscopic vision include a method in which left and right images are displayed alternately using a display device having left and right display sections corresponding respectively to the left and right eyes, and spectacles are used in which the left and right eyes are alternately covered using liquid crystals in synchronization with the alternating display; a method in which left and right images having different directions of polarization are presented simultaneously, and spectacles are used in which the lenses for the left and right eyes are polarized correspondingly; a lenticular display method in which the left and right images are finely divided into sections and interlaced, and then the sections of the left image are displayed with one directionality and the sections of the right image with another directionality, thus allowing stereoscopic vision without the use of spectacles; and a method in which the left and right images are presented separately to the left and right eyes using a head-mounted display.

Moreover, in the present invention, to further accentuate the differences between the left and right images, the colors of the left and right images, i.e. the past and current images, may be changed. X-ray image data is data purely on the intensity of the X-rays, with there being no data relating to color. The images are usually displayed in monochrome, but it is possible, for example, to present a monochrome image having a blue hue to the left eye and a monochrome image having a red hue to the right eye. When the observer fuses the two images, places where the images differ from one another give the observer a feeling of incongruity, which is intensified by the color difference.

Moreover, in the present invention, it is also possible to make one of the images flash on and off when displaying the left and right images. As a result, the observer must carry out image fusion repeatedly, which causes the differences between the images to be seen more clearly.

Moreover, in the present invention, the observer can designate a position on the display screen upon which the two images are displayed, whereupon an indicator mark is displayed in the designated position. Examples in which such indicator marks are displayed will now be described with reference to FIG. 13 and FIG. 14.

Figure 13:
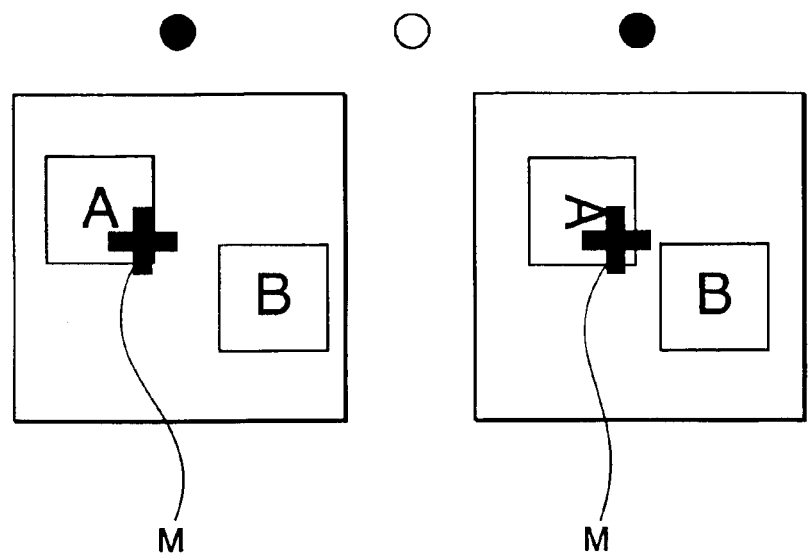
FIG. 13 shows an example in which indicator marks have been put on a display screen that display two images.
Figure 14:
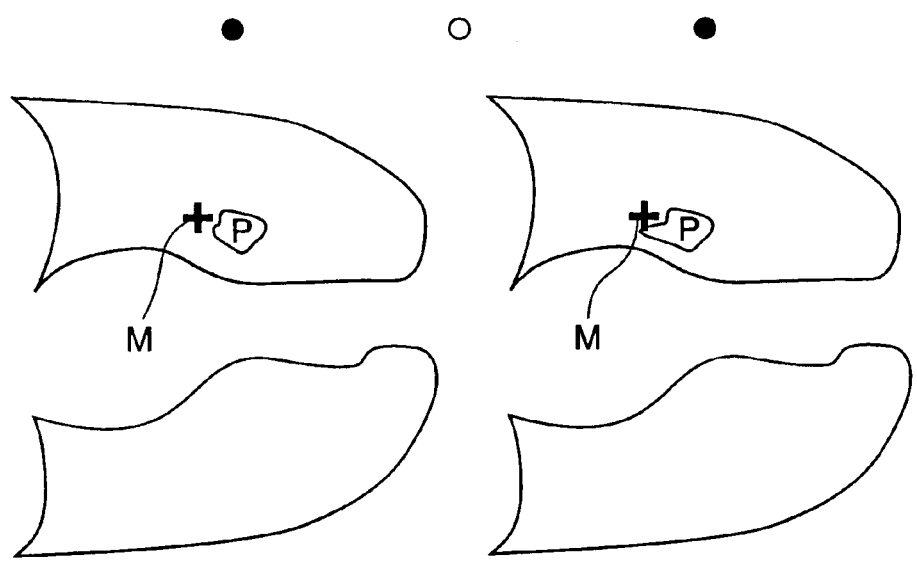
FIG. 14 shows an example in which indicator marks have been put on chest X-ray radiographs displayed rotated through 90 degrees.

FIG. 13 shows an example in which indicator marks have been put on a display screen that displays two images. FIG. 14 shows an example in which indicator marks have been put on chest X-ray images displayed rotated through 90 degrees.

Specifically, as shown in FIG. 13, indicator marks M (+) can be put on the display screen displaying the two images in accordance with operational input from the observer. By looking at the position of the marks M (+) put on the two displayed images, the observer can more easily recognize places where the images differ from one another and confirm the differences. Moreover, as shown in FIG. 14, when viewing two chest X-ray images (past and current images) rotated through 90 degrees, marks M (+) can similarly be put on the chest X-ray images in the position of an object P in the chest, allowing changes in the shape of the object P to be recognized more easily.

Moreover, according to the present invention, at least two further display means for displaying the two images (past and current images) singly are provided, and the two images are displayed on the respective display means. When an indicator mark is put onto the display means displaying the two images together as described above, the mark is also put onto each of the past image and the current image displayed singly. If necessary, the past and current images thus marked can be stored and then viewed again later, when the marks will be of assistance to the observer.

Moreover, in the present invention, the displayed chest X-ray images may be subjected to spatial frequency accentuation processing to accentuate places where there are tumors or the like. The strength of the spatial frequency accentuation processing can be changed by the observer through operational input.

As described above, according to the present invention, two-eyed stereoscopic viewing of two images of the same subject taken at different times allows places where the images differ from one another to be seen clearly. If the present invention is applied to medical images such as chest X-ray images, CT (computed tomography) images, MRI (magnetic resonance imaging) images or ultrasound diagnosis images, then the differences between two medical images of the same subject taken at different times can be seen. It should be noted, however, that differences seen between the two medical images may not necessarily be indicative of disease. Rather, the present invention has the effect of allowing one to find out whether or not there are sites where changes have occured between images, possibly due to disease, and the positions of such sites; this information can be used as supplementary information when making medical diagnoses.

First Embodiment

Figure 1:
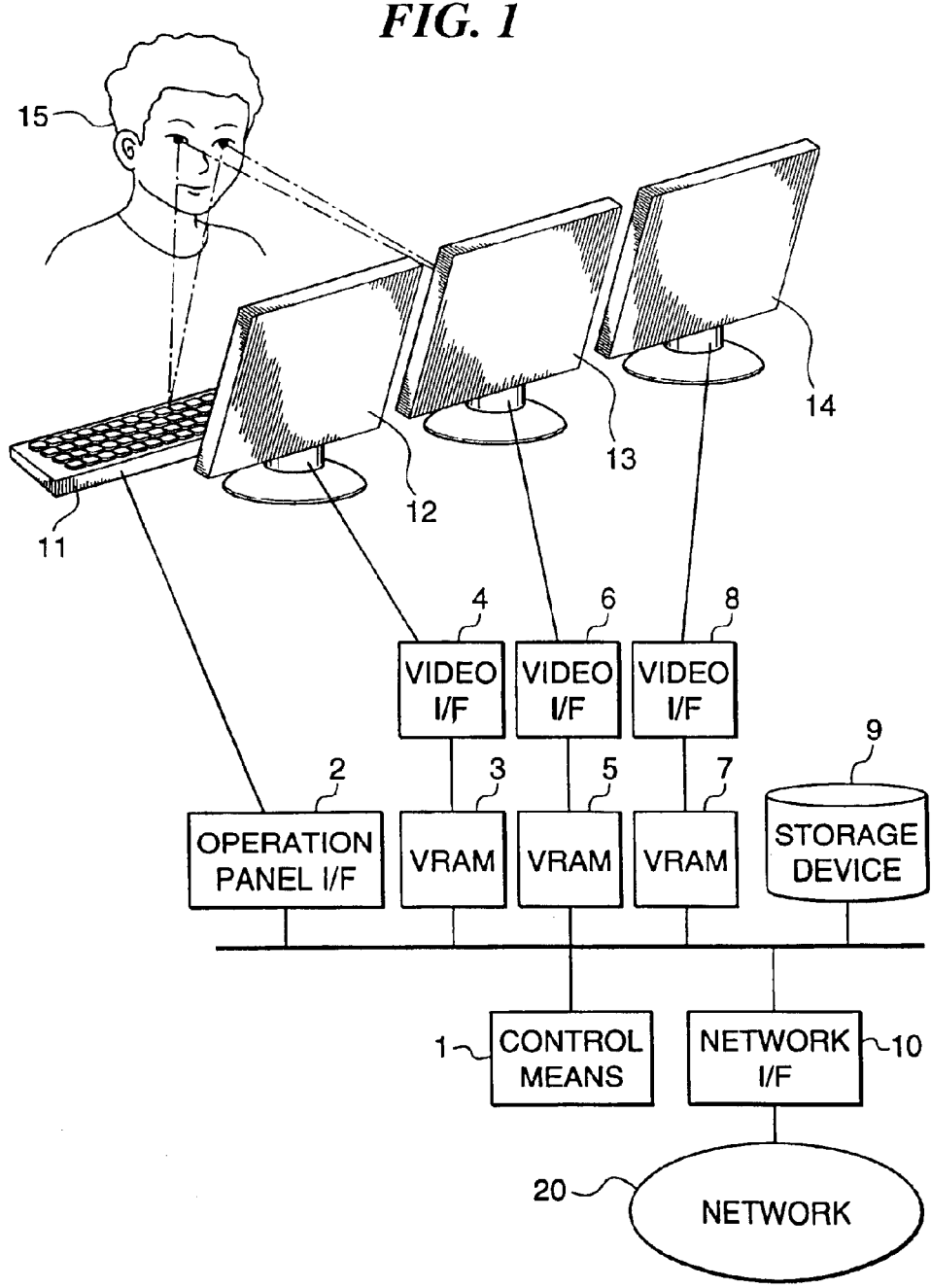
FIG. 1 is a block diagram showing the constitution of an image display apparatus according to a first embodiment of the present invention.

A description will now be given of a first embodiment of the present invention with reference to the drawings. FIG. 1 is a block diagram showing the constitution of an image display apparatus according to the first embodiment. In this embodiment, a description will be given of an image display apparatus for displaying medical images such as chest X-ray images, CT images, MRI images or ultrasound diagnosis images.

The image display apparatus displays at least two medical images such as chest X-ray images taken of the same subject at different times. As shown in FIG. 1, the image display apparatus has a network interface (network I/F) 10 for inputting medical images (including a past image and a current image) and information relating to the patient in question from a network 20.

A chest X-ray radiography device or the like is connected to the network I/F 10 via the network 20. Chest X-ray images taken by the chest X-ray radiography device are transferred along with patient information and the like from the chest X-ray radiography device to the image display apparatus via the network 20.

The chest X-ray radiography device may be, for example, a device that converts the X-ray intensity distribution directly into a digital image using a so-called X-ray flat panel sensor, or a device in which the X-ray intensity distribution is recorded on an X-ray film. The chest X-ray images inputted via the network 20 may be, for example, digital images obtained by scanning a photostimulable fluorescent body called an imaging plate, digital images obtained from a device comprised of a photomultiplier tube and a television camera, or digital images obtained from an X-ray film using a film scanner.

Medical images inputted via the network I/F 10 are stored in a storage device 9 in the form of a database, with this storage being controlled by control means 1, described below. Images taken of the same subject are stored along with additional information indicating that the images are of the same subject and indicating the times when the images were taken. As a result, it is clear that the images correspond to one another, and the amount of time elapsed between the images is known. The storage device 9 is comprised of a hard disk or the like. Desired medical images can be read from the storage device 9, with the reading being controlled by the control means 1.

When, for example, a past chest X-ray image and the corresponding current chest X-ray image of the same subject are read from the storage device 9, the past chest X-ray image is temporarily stored in a VRAM 7 and then sent via a video interface (video I/F) 8 to a display device 14, which displays the past chest X-ray image; the current chest X-ray image is temporarily stored in a VRAM 5 and then sent via a video interface (video I/F) 6 to a display device 13, which displays the current chest X-ray image.

Moreover, the past chest X-ray image and the current chest X-ray image read from the storage device 9 are composited by the control means 1, and the composite image thus obtained is temporarily stored in a VRAM 3 and then sent via a video interface (video I/F) 4 to a stereo display device 12 such as a lenticular display device.

The composite image is displayed on the stereo display device 12 in such a way that the past chest X-ray image and the current chest X-ray image are presented separately to the right and left eyes respectively of an observer 15.

The control means 1 contains a CPU, a ROM, a RAM, a chip set and so on. The CPU carries out overall control of the image display apparatus in accordance with a program stored in the ROM, and also carries out processing such as that for forming the composite image described above. An operation panel 11 that can be operated by the observer 15 is used for inputting commands to the control means 1, for setting modes, and so on.

Various keys for inputting commands, setting modes and so on are provided on the operation panel 11. When a key is pressed, corresponding key information is inputted into the control means 1 via an operation panel interface 2.

When the observer 15 wishes to view the chest X-ray images of a certain patient, the observer 15 carries out operations through the operation panel 11 for reading the corresponding image data from the storage device 9. Here, it shall be assumed that, in accordance with these operations, a past chest X-ray image and a corresponding current chest X-ray image of the same patient are read from the storage device 9, and the two images are composited as described above.

It should, however, be noted that a command for reading the past chest X-ray image, a command for reading the current chest X-ray image, and a command for compositing the two images can also each be sent separately by operating the operation panel 11 accordingly.

When the past and current chest X-ray images of the same patient are read in, the past chest X-ray image is displayed on the display device 14 and the current chest X-ray image on the display device 13. Moreover, a composite image as described above is displayed on the stereo display device 12 in such a way that the past chest X-ray image and the current chest X-ray image are presented separately to the right eye and the left eye respectively of the observer 15. As a result, the observer 15 can fuse the presented images together, perceiving them as a single stereoscopic image. The observer 15 compares the images displayed on the display devices 12, 13 and 14 and looks for changes indicative of disease in the patient in question.

Depending on whether or not the image displayed on the stereo display device 12 can be seen stereoscopically by the observer 15, the displayed image can either be left as it is or can be rotated through, for example, 90 degrees using rotation processing. The choice of whether to rotate or not can be carried out by operational input from the operation panel 11. Moreover, rotation processing for rotating by any chosen angle can be carried out, with it being possible to set the angle of rotation from the operation panel 11.

Furthermore, in addition to the rotation processing described above, other processing is also possible, such as rotation processing in which only one of the left eye image and the right eye image is rotated, shifting processing in which one of the left eye image and the right eye image is shifted in the vertical direction, and magnification processing in which one of the left eye image and the right eye image is enlarged or reduced in size. These types of processing are carried out by the control means 1. Specifically, processing such as image magnification, shifting and rotation can be carried out by the control means 1 controlling the addresses and rate of reading from the VRAM 3. As a result, the left and right eye images can be manipulated until a stereoscopically viewable fused image is obtained.

If, in viewing the images displayed on the stereo display device 12, the observer 15 intuitively perceives any places that cannot be viewed stereoscopically as a feeling of incongruity, he or she can remember where these places are and then look back at the images displayed on the display device 13 (the current chest X-ray image) and the display device 14 (the past chest X-ray image).

If the two images were just viewed separately using only the display devices 13 and 14, then places where there are differences between the two images indicative of disease might not be noticed. However, if the stereo display device 12 is used as described above, then the probability of noticing such places is higher.

Figure 2:
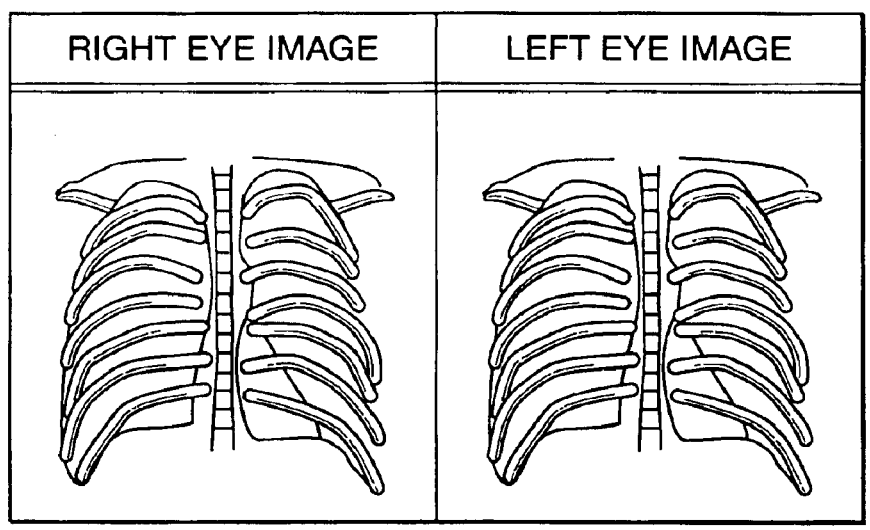
FIG. 2 shows an example of images displayed on a stereo display device 12 of the image display apparatus shown in FIG. 1 under standard operation.

FIG. 2 shows an example of images displayed on the stereo display device 12 of the image display apparatus shown in FIG. 1 under standard operation (i.e. with no rotation processing, shifting processing or magnification processing), while FIGS. 3A to 3D show examples of images displayed on the stereo display device 12 of the image display apparatus shown in FIG. 1 after carrying out rotation processing of two images, rotation processing of one image, shifting processing, and magnification processing, as described above, respectively.

Under standard operation, the image captured by the right eye is displayed on the left side and the image captured by the left eye on the right side of the stereo display device 12, as shown in FIG. 2. That is, the observer 15 sees the image on the left side with his/her right eye and the image on the right side with his/her left eye.

Figure 3A:
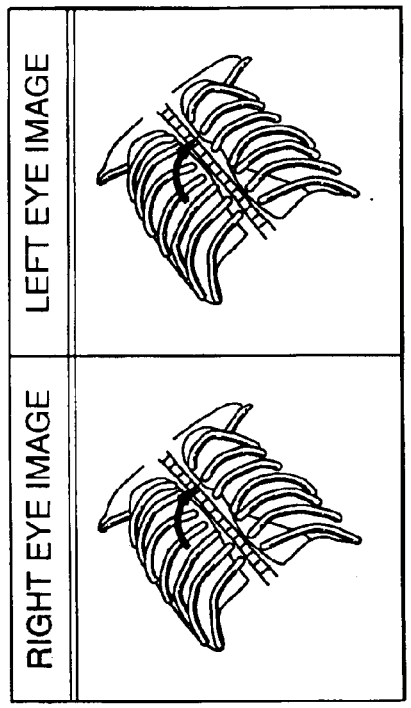
FIGS. 3A to 3D show examples of images displayed on the stereo display device 12 of the image display apparatus shown in FIG. 1 after carrying out rotation processing of two images, rotation processing of one image, shifting processing, and magnification processing, respectively.
Figure 3B:
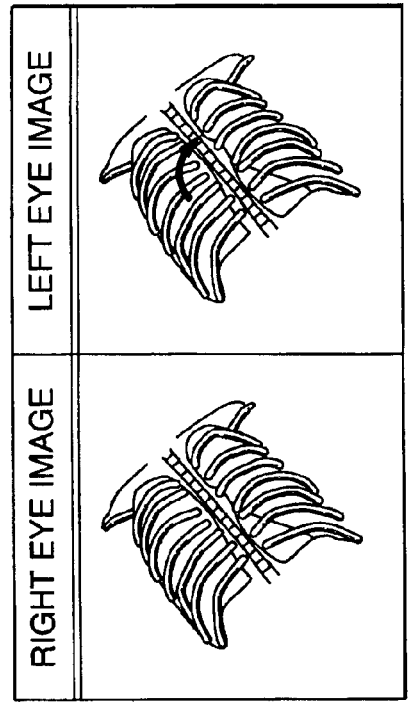
Figure 3C:
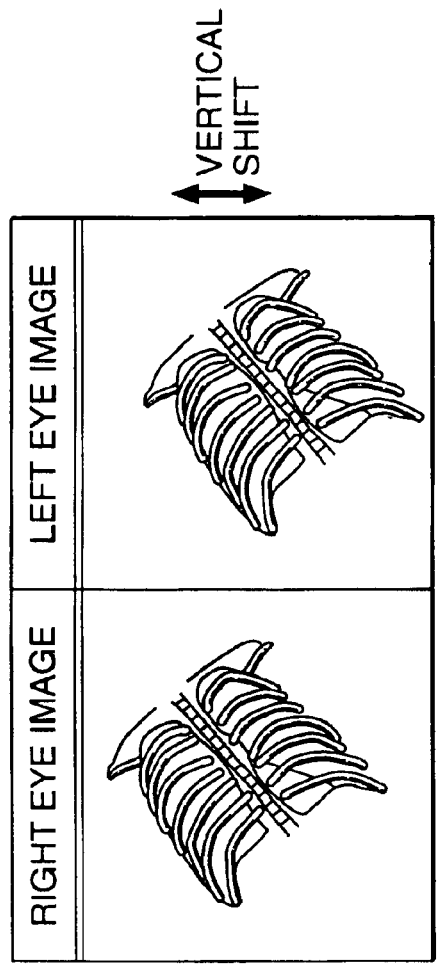
Figure 3D:
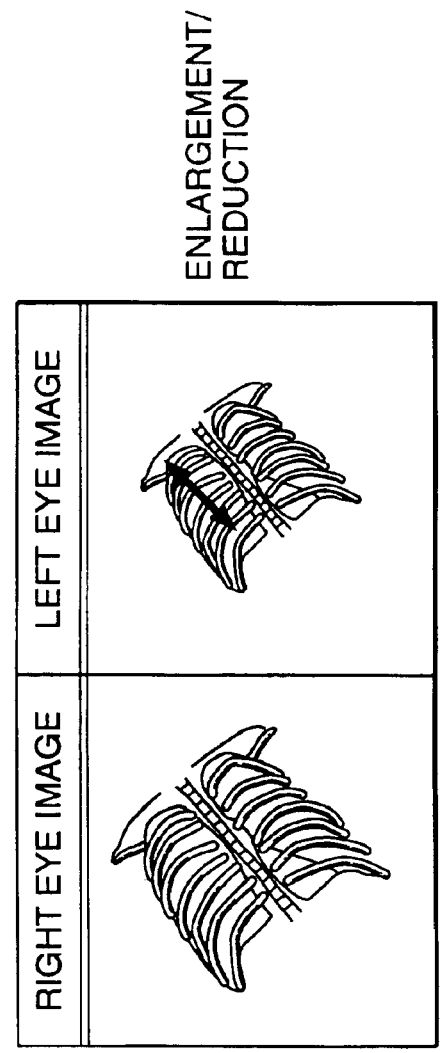

The observer 15 operates the operation panel 11 while viewing the displayed images. By operating the operation panel 11, simple image processing can be carried out interactively to make any differences between the two images (the past and current chest X-ray images) easily visible; for example, both images can be rotated as shown in FIG. 3A, one of the images can be rotated as shown in FIG. 3B, the position of one of the images can be corrected by shifting vertically as shown in FIG. 3C, or one of the images can be enlarged or reduced in size as shown in FIG. 3D.

Specifically, the observer 15 operates the operation panel 11 to carry out image processing such that the two images are as far as possible fused into a single stereoscopic image rather than such that the two images are seen overlapping one another.

It is possible to not only carry out processing relating to the positions, orientations and sizes of the left and right images, but, again using the control means 1, also to change the display brightness and the like of the two images independently. Moreover, in terms of the technical concept of the present invention, it is also possible to implement more advanced image processing in which an image segment is designated and warping is carried out on the designated image segment.

The reason that such rotation, shifting, magnification and brightness adjustment are necessary is that the position of the patient's body during the X-ray radiography and the radiographic conditions may be different for each of the X-ray images. For example, if the past image is an analog image that was taken using an old-style film screen system and then digitized by scanning the film using a film scanner, then the size of the image may well be different to that of the current image.

As described above, according to the present embodiment, subtle differences between two images of the same subject obtained at different times can be clearly shown to the observer 15 without carrying out complex image processing.

It should also be noted that, although in the present embodiment a stereo display device 12 such as a lenticular display device that can be viewed without spectacles was used, the present invention is not limited to such a display device. Any display device that projects separate images to the left and right eyes of the observer and thus allows stereoscopic viewing may be used, for example a time division type display device that uses liquid crystal shutter spectacles, a display device that uses polarizing spectacles, or a display device that uses a head-mounted display.

Figure 15B:
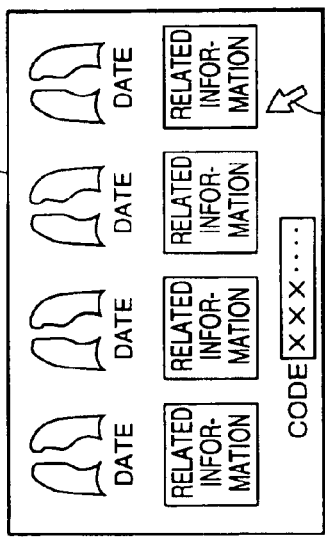
FIGS. 15A to 15D show screens for searching for and selecting images to be displayed according to any of the embodiments of the present invention.
Figure 15D:
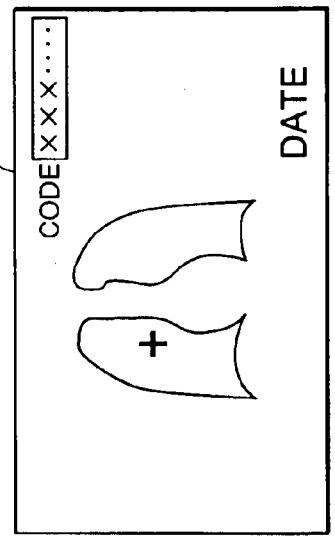
Figure 15A:
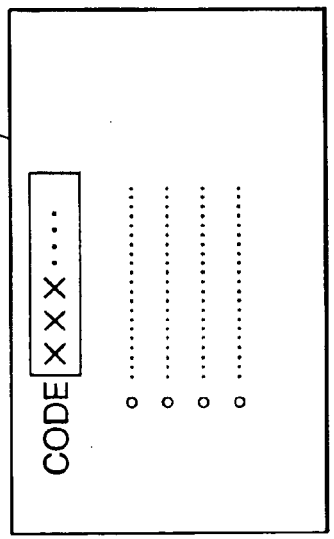
Figure 15C:
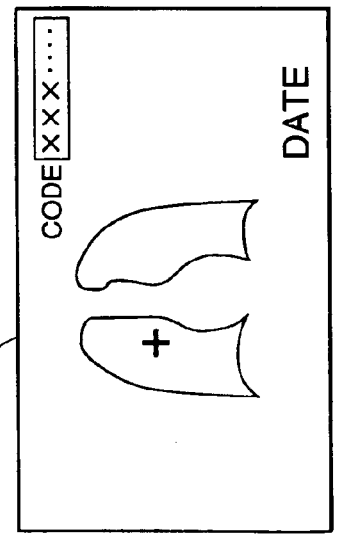

A description will now be given, with reference to FIGS. 15A to 15D, of an example of a series of operations carried out by the observer 15 using the operation panel 11 to display chest X-ray images or the like on the display devices 12, 13 and 14. The observer 15 first uses the operation panel 11 to send a search command, whereupon the control means 1 switches the display on, for example, the display device 13 or the display device 14 over to a search screen, as shown in FIG. 15A. The observer 15 now uses the operation panel 11 to input a patient's name or code onto the search screen, whereupon the control means 1 reads images such as chest X-ray images corresponding to the inputted name or code from the storage device 9, and displays the read images as a list of images or a list of reduced images or the like along with the date when each image was taken and other related medical information, as shown in FIG. 15B. The observer 15 uses a mouse or the like to move a pointer P over the display screen shown in FIG. 15B and select desired images, whereupon the selected images are displayed on the display devices 13 and 14, as shown in FIGS. 15C and 15D. A composite image formed from the two selected images as described earlier is also displayed on the stereo display device 12.

As a result of the above, the two images taken at different times can be compared and places where changes have occurred can be found, thus allowing changes in the patient's medical condition or the like to be perceived in a more visual way than conventionally.

Second Embodiment

Figure 4:
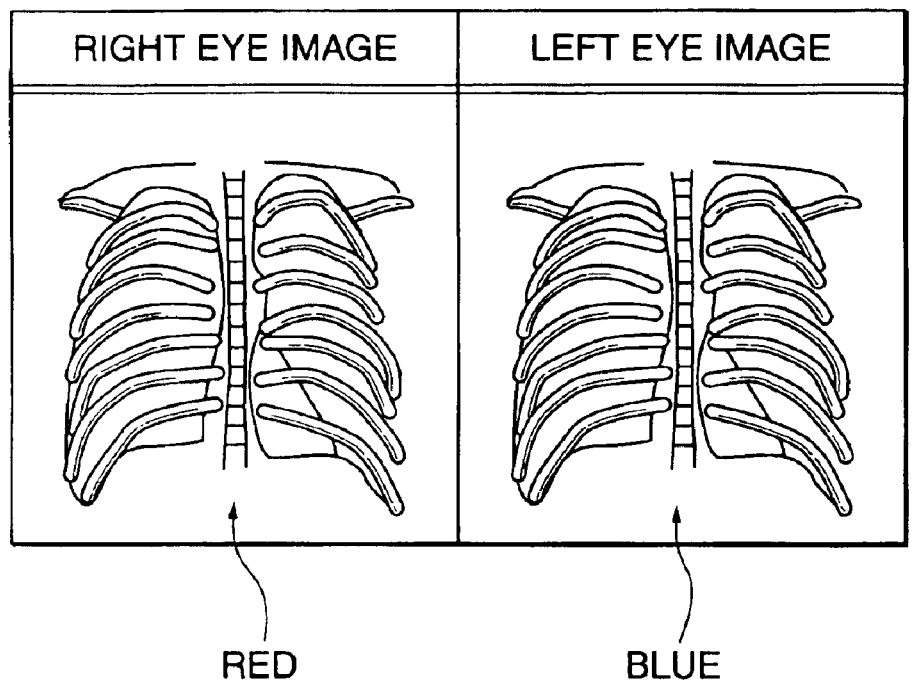
FIG. 4 shows an example of images displayed on a stereo display device of an image display apparatus according to a second embodiment of the present invention.

A description will now be given of a second embodiment of the present invention with reference to FIG. 4. FIG. 4 shows an example of images displayed on a stereo display device of an image display apparatus according to the second embodiment. In FIG. 4, the image captured by the right eye is shown on the left side and the image captured by the left eye on the right side. The image display apparatus has the same constitution in the present embodiment as in the first embodiment described above, and hence the description of this constitution will be omitted here.

The present embodiment differs from the first embodiment in that there is a function for displaying the left and right eye images in different colors.

For example, the right eye image may be displayed in red on the stereo display device 12 and the left eye image in blue, as shown in FIG. 4. The colors used can be freely changed in accordance with the preference of the observer 15. The chosen colors are displayed, for example, using combinations of red, green and blue.

When the two images having different colors are viewed stereoscopically by the observer 15, a stronger feeling of incongruity is sensed in places where the images differ from one another (i.e. places where it is difficult to achieve stereoscopic vision) than in the first embodiment, in which only the images themselves differed but the colors were the same. Differences between the two images are thus more easily perceived than in the first embodiment.

In actual practice, it may be difficult for the observer 15 to fuse the left and right eye images together if the colors of the two images are different from the start. In such a case, the left and right eye images are first both displayed in black and white, and the observer 15 then carries out rotation, shifting, magnification and so on as described above in the first embodiment until the two images can be fused together into a single stereoscopic image. Once fusion has been achieved, the observer 15 then gradually changes the colors of the two images, for example making the current image blue and the past image red, while continuing to view the fused image. As a result, the fused state that was obtained while viewing in black and white is maintained. Once the displayed images have become completely red and blue respectively, the observer 15 makes observations and a diagnosis.

Third Embodiment

Figure 5:
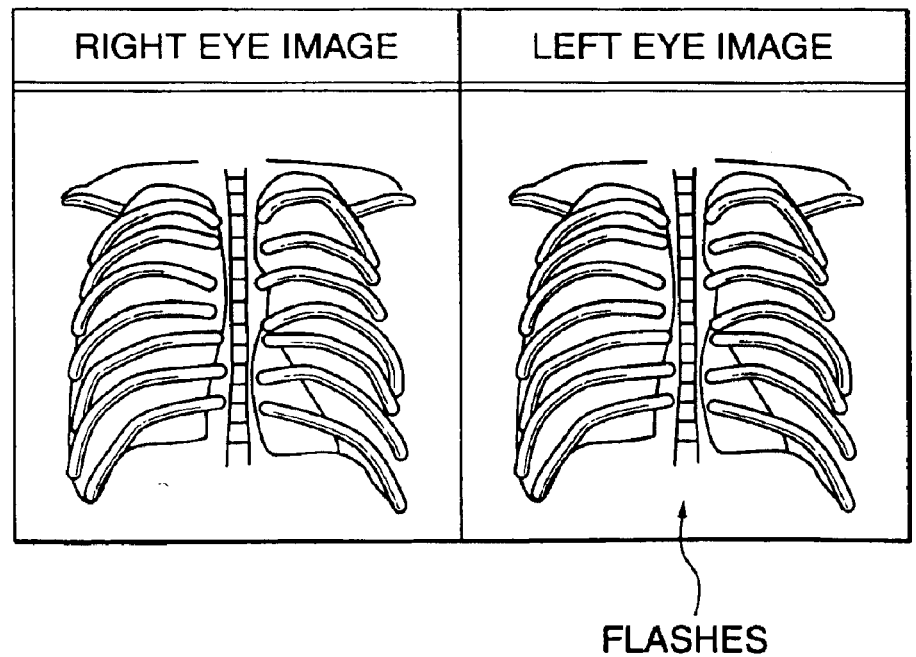
FIG. 5 shows an example of images displayed on a stereo display device of an image display apparatus according to a third embodiment of the present invention.

A description will now be given of a third embodiment of the present invention with reference to FIG. 5. FIG. 5 shows an example of images displayed on a stereo display device of an image display apparatus according to the third embodiment. In FIG. 5, the image captured by the right eye is shown on the left side and the image captured by the left eye on the right side. The image display apparatus has the same constitution in the present embodiment as in the first embodiment described above, and hence the description of this constitution is omitted here.

The present embodiment differs from the first or second embodiment in that there is a function for making either the left eye image or the right eye image flash on and off. For example, in FIG. 5, the left eye image can be made to flash. The rate of flashing can be freely changed by the observer 15.

This flashing is effective particularly when the colors of the two images are changed as in the second embodiment. If one of the images is made to flash relatively slowly (for example at about 1 second intervals), then places where the images differ from one another are seen by the observer 15 as an afterimage, and hence it becomes easier to notice such places.

It is also effective, for example, to alternate the left eye image with the right eye image rather than making the left eye image flash on and off.

In the present embodiment, the left eye image was made to flash, but it goes without saying that the same effect is achieved if the right eye image is made to flash instead.

The processing for making one of the images flash or changing the colors of the images can be carried out by the control means 1 using known methods.

Fourth Embodiment

Figure 6:
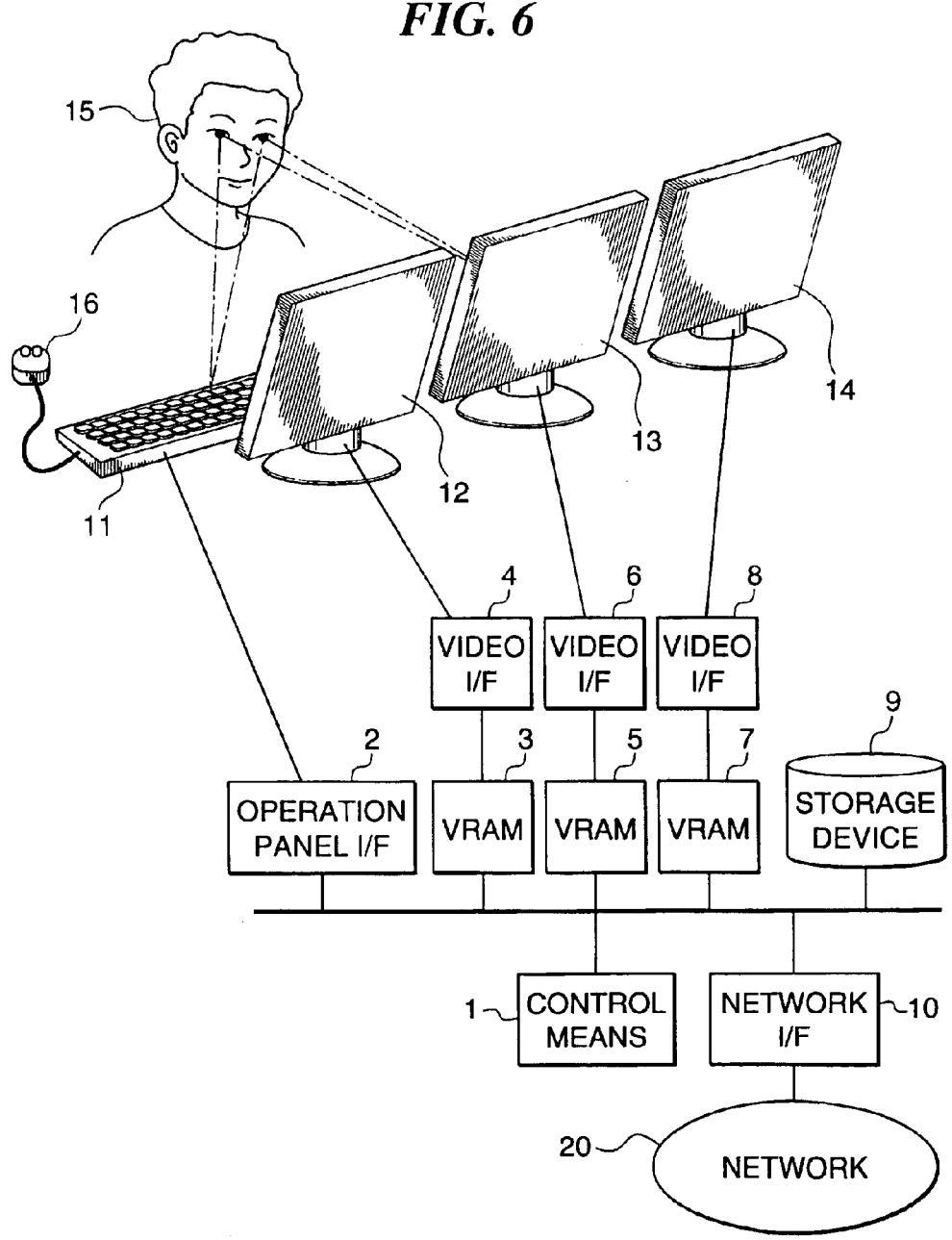
FIG. 6 is a block diagram showing the constitution of an image display apparatus according to a fourth embodiment of the present invention.
Figure 7:
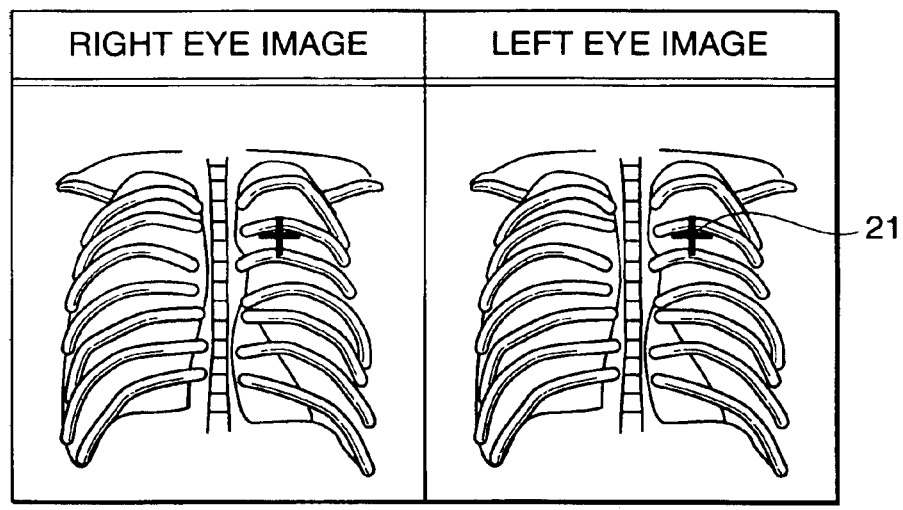
FIG. 7 shows an example in which images displayed on the stereo display device 12 of the image display apparatus shown in FIG. 6 have been subjected to marking.

A description will now be given of a fourth embodiment of the present invention with reference to FIGS. 6 and 7. FIG. 6 is a block diagram showing the constitution of an image display apparatus according to the fourth embodiment. FIG. 7 shows an example in which images displayed by the stereo display device 12 of the image display apparatus shown in FIG. 6 have been subjected to marking.

In FIG. 6, blocks having the same functions as in the first embodiment are designated by the same reference numerals as in the first embodiment; the description of these blocks will either be abbreviated or omitted altogether here.

In contrast with the first embodiment, in the present embodiment there is a mouse 16 for designating a position on the display screen of the stereo display device 12, as shown in FIG. 6. In the present embodiment, it is possible for the control means 1 to put a mark on the display screen of the stereo display device 12 in a position freely chosen using the mouse 16. Specifically, when the position on the display screen is designated, control is carried out such that a mark is placed on each of the two images in the designated position on the display screen and each of the two images is displayed with the mark superposed thereon.

When the observer 15 intuitively perceives a place where there is a feeling of incongruity from the images displayed on the stereo display device 12, he or she operates the mouse 16 to move a pointer 21 on the stereo display device 12 and thus mark the position of the place where the feeling of incongruity was sensed, as shown in FIG. 7. At this time, similar marks are also placed in the position in question on the current image displayed on the display device 13, which corresponds to the right eye image displayed on the stereo display device 12, and the past image displayed on the display device 14, which corresponds to the left eye image displayed on the stereo display device 12. The observer 15 can then look back at the current image displayed on the display device 13 and the past image displayed on the display device 14 using normal vision, and make a diagnosis based on the marks on the display device 13 and the display device 14. As a result, the probability of detecting places where changes indicative of disease have occured is higher than if the observer 15 had merely viewed the current image and the past image normally (i.e. without using the stereo display device 12), when such places might not have been noticed.

Moreover, when marks have been put on the separately displayed past image and current image, if necessary the marked past image and current image can be stored in the storage device 9, so that when the images are subsequently retrieved and viewed once again, the marks are of assistance to the observer.

Fifth Embodiment

Figure 8:
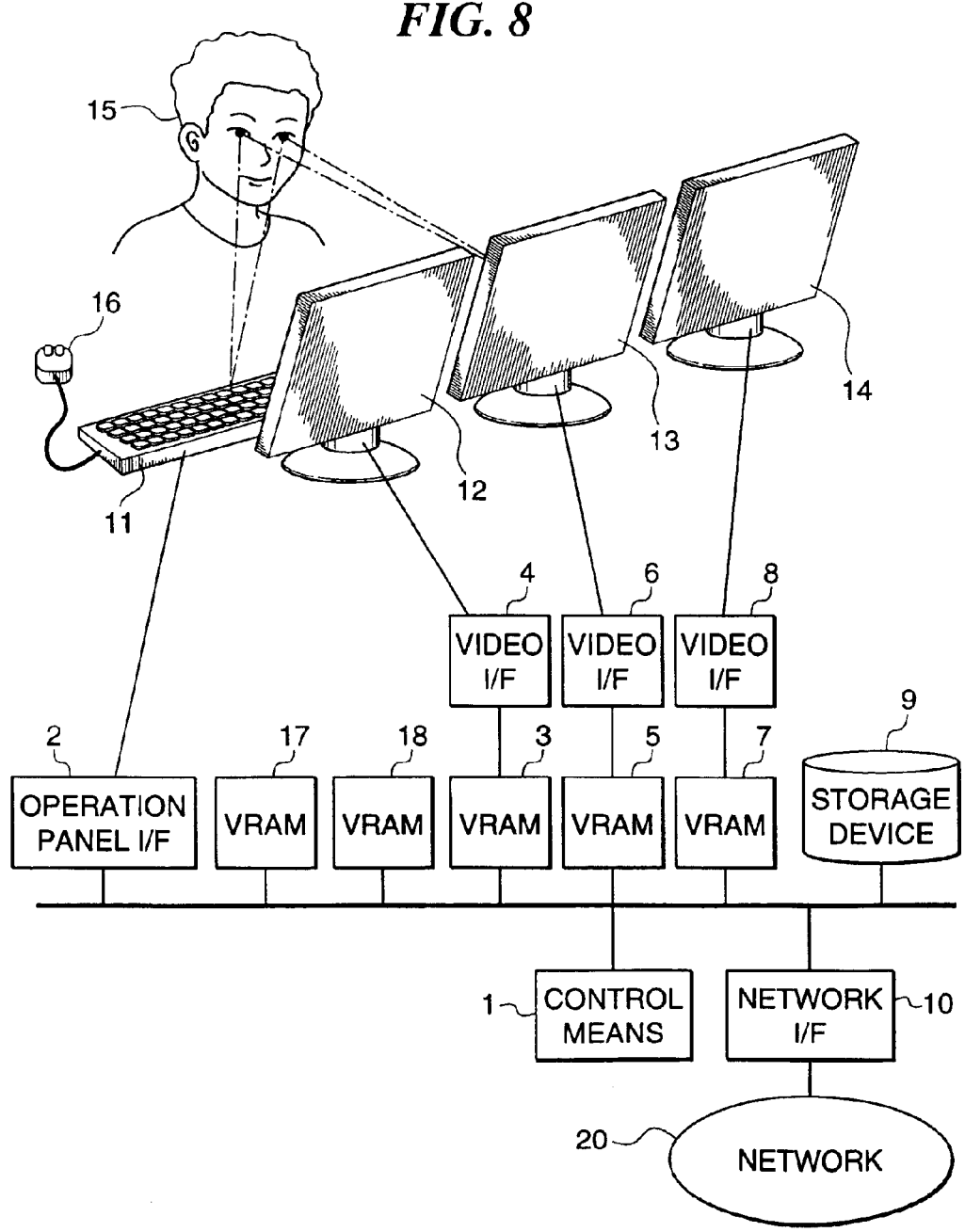
FIG. 8 is a block diagram showing the constitution of an image display apparatus according to a fifth embodiment of the present invention.

A description will now be given of a fifth embodiment of the present invention with reference to FIG. 8. FIG. 8 is a block diagram showing the constitution of an image display apparatus according to the fifth embodiment. In FIG. 8, blocks having the same functions as in the first embodiment are designated by the same reference numerals as in the first embodiment; the description of these blocks will either be abbreviated or omitted altogether here.

The present embodiment differs from the first embodiment in that it is possible to subject the chest X-ray images to spatial frequency accentuation processing and then display the chest X-ray images thus processed on the stereo display device 12.

Moreover, it is possible for the spatial frequency intensity of the spatial frequency accentuation processing to which the chest X-ray images are subjected to be changed in accordance with operational input from the observer 15.

A method of accentuating an image by frequency is called unsharp masking. In this method, representing the initially obtained image by G and the image after subjecting to unsharp processing (blurring) by Gu, a new processed image Gm is produced in accordance with the following formula (1) using an accentuation degree coefficient a.

$$Gm = G + a \cdot (G - Gu) \qquad (1)$$

The accentuation degree coefficient a is a positive variable. The larger the value, the more the high spatial frequency domain is accentuated. A common method of creating Gu is to use for each targeted pixel the mean value of the pixels in a region surrounding that targeted pixel. The spatial frequency domain that is accentuated is determined by the size of this surrounding region.

Referring to FIG. 8, in the present embodiment, unsharp processing as described above is carried out by the control means 1, and a VRAM 17 and a VRAM 18 are provided for storing the unsharp images computed for the current chest X-ray image and the past chest X-ray image respectively. As well as computing the unsharp images for the current and past chest X-ray images, the control means 1 carries out computations in accordance with the above-mentioned formula (1) using the computed unsharp images to obtain new current and past chest X-ray images, and composites the two new images. The composite image, which will be displayed on the stereo display device 12, is stored in the VRAM 3.

As a result of the above, it is possible for the observer 15 to stereoscopically view the chest X-ray images with improved sharpness. Moreover, while viewing the images, the observer 15 can carry out operations to change a numerical value corresponding to the accentuation degree coefficient a. The observer 15 can thus change the value of the accentuation degree coefficient a interactively so that differences between the current and past chest X-ray images can be seen more clearly. Places where a feeling of incongruity is sensed can also be marked as was shown in FIG. 7.

In the embodiments described above, examples have been given of some possible combinations of the types of processing that can be carried out in the present invention. However, the present invention is not limited to these combinations. Moreover, when displaying the past and current images, a differential image between the past and current images can also be presented to the observer at the same time, further improving the probability of changes indicative of disease being detected.

Moreover, in the embodiments described above, examples have been given in which the present invention is applied to medical images such as chest X-ray images. However, the present invention is not limited to medical images, but rather can be applied to the intuitive detection of differences between any two images.

Furthermore, the present invention can either be realized using dedicated display devices or using a personal computer, a workstation or the like.

Furthermore, in the embodiments described above, the display processing in the image display apparatus is carried out in accordance with a program stored in a ROM of the control means 1, but the program may instead be supplied stored on a storage medium such as a ROM, a DVD-ROM, a CD-ROM or a memory card. In such a case, a CPU reads the program from the storage medium and executes the program to achieve the purposes of the present invention. The storage medium on which the program is stored thus constitutes the present invention.

According to the embodiments of the present invention described above, display means is controlled to display the two images such that two images of the same subject obtained at different times are projected separately to the left and right eyes of an observer. As a result, subtle differences between the two images of the same subject obtained at different times can be clearly shown to the observer without carrying out complex image processing.

Moreover, by marking places where a feeling of incongruity is sensed, places where the two images differ from one another can be shown more clearly.

Furthermore, by subjecting chest X-ray images to spatial frequency accentuation processing and then displaying the chest X-ray images thus processed on the display means, places where changes indicative of disease have occured are accentuated, and the chest X-ray images can be viewed stereoscopically with improved sharpness, thus allowing places where the images differ from one another to be identified more clearly.

Furthermore, if the colors of the two images are changed independently while displaying the two images on the display means, then a stronger feeling of incongruity is sensed in places where the two images differ from one another, and hence it becomes easier to perceive differences between the two images.

Furthermore, if one of the two images is made to flash while displaying the two images on the display means, then places where the images differ from one another are seen by the observer as an after-image, and hence it becomes easier to notice such places.

Furthermore, if processing is carried out in which at least one of the two images displayed on the display means is rotated, magnified or shifted on the display screen of the display means (possibly while also independently changing the colors of the two images or making one of the two images flash as described above), then the observer can obtain a clearer stereoscopic image.

Furthermore, if the two images are marked as described above and then stored separately along with position information indicating the position of the mark, then when the images are subsequently retrieved and viewed once again, the marks will be of assistance to the observer.

What is claimed is:

1. An image display apparatus comprising:
   input means for inputting two images of a same subject obtained at different times;
   display means for displaying the two inputted images on a display screen in a manner enabling an observer to fuse the two inputted images together for stereoscopic viewing;
   display control means for controlling said display means to display the two inputted images such that the two inputted images we displayed separately into left and right eyes of the observer; and
   position designation means for designating a position on the display screen of said display means in accordance with operational input from the observer,
   wherein said display control means is responsive to a position being designated by said position designation means, for controlling said display means to display a mark in the designated position on the display screen of said display means in a manner being superposed on each of the two images.

2. An image display apparatus as claimed in claim 1, wherein each of the two images is an image produced from a radiation intensity distribution.

3. An image display apparatus as claimed in claim 2, wherein the two images are a past image and a current image taken of the same human subject.

4. An image display apparatus as claimed in claim 3, comprising spatial frequency accentuation means for carrying out spatial frequency accentuation processing on the images, and wherein said display control means controls said display means to display the images subjected to the spatial frequency accentuation processing.

5. An image display apparatus as claimed in claim 4, comprising spatial frequency intensity setting means for setting a spatial frequency intensity of said spatial frequency accentuation processing in accordance with operational input from the observer, and wherein said spatial frequency accentuation means carries out the spatial frequency accentuation processing on the images at the set spatial frequency intensity.

6. An image display apparatus as claimed in claim 4, wherein said display means has a color display function, and said display control means controls said display means to display the two images while changing colors of the two images independently.

7. An image display apparatus as claimed in claim 4, wherein said display control means controls said display means to display the two images while making one of the two images flash.

8. An image display apparatus as claimed in claim 7, wherein a flashing interval at which the one of the two images is made to flash is variable.

9. An image display apparatus as claimed in claim 4, wherein said display means has a display screen, and wherein said display control means controls said display means to carry out rotating, magnifying and shifting at least one of the two images on the display screen of said display means.

10. An image display apparatus as claimed in claim 1, comprising at least two single image display means for displaying each of the two images singly, and wherein said display control means controls said single image display means to display each of the two images singly.

11. An image display apparatus as claimed in claim 10, wherein each of said single image display means has a display screen, the image display apparatus comprising position designation means for designating a position on the display screen of said display means in accordance with operational input from the observer, and wherein said display control means is responsive to a position being designated by said position designation means, for controlling said display means to display a mark in the designated position on the display screen of said display means in a manner being superposed on each of the two images, and wherein, when the mark is displayed in the position designated by said position designation means on the display screen of said display means, said display control means controls said single image display means to also display the mark in a position corresponding to the designated position on the display screen of each of said at least two single image display means.

12. An image display apparatus as claimed in claim 11, comprising storage means for separately storing each of the two images along with position information indicating the corresponding position of the mark.

13. An image display method of displaying two images of a same subject obtained at different times on display means in a manner such that an observer can fuse the two images together for stereoscopic viewing, the method comprising the steps of:
   inputting the two images;
   controlling said display means to display the two inputted images such that the two inputted images are displayed separately into left and right eyes of the observer, and the observer can fuse the images together;

designating a position on a display screen of said display means in accordance with operational input from the observer, and controlling, in response to the position being designated by said position designation step, said display means to display a mark in the designated position on the display screen of said display means in a manner being superposed on each of the two images.

14. An image display method as claimed in claim 13, wherein each of the two images is an image produced from a radiation intensity distribution.

15. An image display method as claimed in claim 14, wherein the two images are a past chest X-ray image and a current chest X-ray image taken of the same human subject.

16. An image display method as claimed in claim 15, comprising a step of carrying out spatial frequency accentuation processing on the chest X-ray images, and wherein said display means is controlled to display the chest X-ray images subjected to said spatial frequency accentuation processing.

17. An image display method as claimed in claim 16, comprising a step of setting a spatial frequency intensity of said spatial frequency accentuation processing in accordance with operational input from the observer, and wherein said spatial frequency accentuation processing is carried out on the chest X-ray images at the set spatial frequency intensity.

18. An image display method as claimed in claim 13, wherein said display means has a color display function, and said display means is controlled to display the two images on said display means while changing colors of the two images independently.

19. An image display method as claimed in claim 13, wherein said display means is controlled to display the two images while making one of the two images flash.

20. An image display method as claimed in claim 19, wherein a flashing interval at which the one of the two images is made to flash is variable.

21. An image display method as claimed in claim 13, wherein said display means is controlled to carry out rotating, magnifying and shifting at least one of the two images on the display screen of said display means.

22. An image display method as claimed in claim 13, wherein at least two single image display means for displaying each of the two images singly are provided, and the image display method further comprises a step of controlling each of said single image display means to display a corresponding one of the two images singly.

23. An image display method as claimed in claim 13, wherein at least two single image display means for displaying each of the two images singly are provided, and the image display method comprises steps of displaying each of the two images singly on a corresponding one of said single image display means, and also displaying the mark in a position corresponding to the designated position on a display screen of each of said single image display means, when the mark is displayed in the designated position on the display screen of said display means.

24. An image display method as claimed is claim 13, further comprising a step of separately storing each of the two images along with position information indicating the corresponding position of the mark.

25. A storage medium storing, so as to be readable by an information processing apparatus, a program for constructing an image display system for displaying two images of a same subject obtained at different times on display means in a manner such that an observer can fuse the two images together for stereoscopic viewing, the program comprising:

an input module for inputting the two images; and a display control module for controlling said display means to display the two inputted images such that the two inputted images are displayed separately into left and right eyes of the observer and the observer can fuse the images together; and a position designation module for designating a position on a display screen of said display means m accordance with operational input from the observer, wherein, in response to the position being designated by said position designation module, said display control module controls said display means to display a mark in the designated position on the display screen of said display means in a manner being superposed on each of the two images.

26. A storage medium as claimed in claim 25, wherein each of the two images is an image produced from a radiation intensity distribution.

27. A storage medium as claimed in claim 25, wherein the two images are a past chest X-ray image and a current chest X-ray image taken of the same human subject.

28. A storage medium as claimed in claim 27, wherein said program comprises a spatial frequency accentuation module for carrying out spatial frequency accentuation processing on the chest X-ray images, and said display control module controls said display means to display the chest X-ray images subjected to said spatial frequency accentuation processing.

29. A storage medium as claimed in claim 28, wherein said program comprises a spatial frequency intensity setting module for setting a spatial frequency intensity of said spatial frequency accentuation processing in accordance with operational input from the observer, and wherein said spatial frequency accentuation module carries out the spatial frequency accentuation processing on the chest X-ray images at the set spatial frequency intensity.

30. A storage medium as claimed in claim 25, wherein said display means has a color display function, and said display control module includes program instructions for controlling said display means to display the two images while changing colors of the two images independently.

31. A storage medium as claimed in claim 25, wherein said display control module includes program instructions for controlling said display means to display the two images on said display means while waking one of the two images flash.

32. A storage medium as claimed in claim 25, wherein said display control module includes program instructions for controlling said display means to carry out rotating, magnifying and shifting at least one of the two images on the display screen of said display means.

33. A storage medium as claimed in claim 25, wherein said display means has a color display function and said display control module includes program instructions for controlling said display means to display the two images while changing colors of the two images independently, program instructions for controlling said display means to display the two images while making one of the two images flash, and program instructions for controlling said display means to carry out rotating, magnifying and shifting at least one of the two images on the display screen of said display means.

34. A storage medium as claimed in claim 25, wherein at least two single image display means for displaying each of the two images singly are provided, and said display control module carries out display processing for controlling each of said single image display means to display a corresponding one of the two images singly.

35. A storage medium as claimed in claim 25, wherein at least two single image display means for displaying each of the two images singly are provided, and said display control module carries out display processing for controlling each of said single image display means to display a corresponding one of the two images singly, and, when the mark is displayed in the designated position on the display screen of said display means, also carries out processing for controlling said single image display means to also display the murk in a position corresponding to the designated position on a display screen of each of said single image display means.

36. A storage medium as claimed in claim 25, wherein said program comprises a storage module for separately storing each of the two images along with position information indicating the corresponding position of the mark.

37. An image display apparatus comprising:

storage means for storing a plurality of images of a same subject along with information relating to a correspondence relationship between the images and times when the images were taken;

searching means for searching for images forming a stereo image and having a correspondence relationship therebetween from the plurality of images stored in said storage means, based on the information;

display means for displaying two of the images in a manner enabling an observer to fuse the two images together for stereoscopic viewing; and display control means for reading any two of the images from said storage means and controlling said display means to display the read two images.

38. An image display apparatus as claimed in claim 37, wherein said display control means includes image processing means for carrying out different image processing on each of the two images displayed on said display means.

39. An image display apparatus as claimed in claim 38, wherein said image processing means carries out processing to make the two images different in color.

40. An image display apparatus as claimed in claim 38, wherein said image processing means carries out processing to make one of the two images flash.

41. An image display apparatus as claimed in claim 37, wherein said display control means causes search results from said searching means to be displayed as a list of reduced images, and controls said display means to stereoscopically display two images selected from the displayed list.

42. An image display method comprising:

a storage step of storing a plurality of images of a same subject along with information relating to a correspondence relationship between the images and times when the images were taken;

a searching step of searching for images forming a stereo image and having a correspondence relationship therebetween from the stored images, based on the information;

a first display step of displaying results of the search; and a second display step of display any two images selected from the search results so as to be viewable as a stereoscopic image.

43. An image display method as claimed in claim 42, wherein said second display step includes an image processing step of carrying out different image processing on each of the two images.

44. An image display method as claimed in claim 43, wherein said image processing step comprises carrying out processing to make the two images different in color.

45. An image display method as claimed in claim 43, wherein said image processing step comprises carrying out processing to make one of the two images flash.

46. An image display method as claimed in claim 43, wherein said first display step comprises displaying the search results as a list of reduced images, and said second display step comprises stereoscopically displaying two images selected from the displayed list.

* * * * *

UNITED STATES PATENT AND TRADEMARK OFFICE
CERTIFICATE OF CORRECTION

PATENT NO. : 6,853,357 B2
DATED : February 8, 2005
INVENTOR(S) : Hitoshi Inoue et al.

It is certified that error appears in the above-identified patent and that said Letters Patent is hereby corrected as shown below:

<u>Column 5,</u>
Line 23, delete "differ-from" and insert -- differ from --.

<u>Column 15,</u>
Line 51, delete "images we displayed" and insert -- images are displayed --.

<u>Column 18,</u>
Line 48, delete "while waking" and insert -- while making --.

Signed and Sealed this

Fourteenth Day of March, 2006

JON W. DUDAS
*Director of the United States Patent and Trademark Office*